United States Patent
Kim et al.

(10) Patent No.: US 8,536,178 B2
(45) Date of Patent: Sep. 17, 2013

(54) PHARMACEUTICAL COMPOSITION FOR PREVENTING OR TREATING DISEASES ASSOCIATED WITH BETA-AMYLOID ACCUMULATION CONTAINING MORPHOLIN OR PIPERAZINE BASED COMPOUNDS HAVING SO₃H OR COOH AS ACTIVE INGREDIENT

(75) Inventors: Dong Jin Kim, Gyeonggi-Do (KR); YoungSoo Kim, Gyeonggi-Do (KR); Hye Yun Kim, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 289 days.

(21) Appl. No.: 12/960,977

(22) Filed: Dec. 6, 2010

(65) Prior Publication Data
US 2011/0144111 A1  Jun. 16, 2011

(30) Foreign Application Priority Data
Dec. 11, 2009 (KR) ........................ 10-2009-0123355

(51) Int. Cl.
*A61K 31/497* (2006.01)
*C07D 241/04* (2006.01)
*C07D 295/00* (2006.01)

(52) U.S. Cl.
USPC ..................... 514/252.12; 544/358

(58) Field of Classification Search
USPC ..................... 514/252.12; 544/358
See application file for complete search history.

(56) References Cited

U.S. PATENT DOCUMENTS
5,840,294 A * 11/1998 Kisilevsky et al. ........ 424/78.31
2001/0051642 A1 * 12/2001 Ahn et al. ................. 514/341

FOREIGN PATENT DOCUMENTS
WO   2004/113277 A2   12/2004

OTHER PUBLICATIONS

Seubert, P., C. Vigo-Pelfrey, et al., "Isolation and quantification of soluble Alzheimer's β-peptide from biological fluids", (1992) *Nature* 359(6393): 325-7.
Shoji, M., T. E. Golde, et al., "Production of the Alzheimer amyloid β protein by normal proteolytic processing", (1992) *Science* 258(5079): 126-9.
Busciglio, J., D. H. Gabuzda, et al., "Generation of β-amyloid in the secretory pathway in neuronal and nonneuronal cells", (1993) *Proc Natl Acad Sci USA* 90(5): 2092-6.
Walsh, D. M., I. Klyubin, et al., "Naturally secreted oligomers of amyloid β protein potently inhibit hippocampal long-term potentiation in vivo", (2002) *Nature* 416(6880): 535-9.
Stine, W. B., Jr., K. N. Dahlgren, et al., "In vitro characterization of conditions for amyloid-β peptide oligomerization and fibrillogenesis", (2003) *J Biol Chem* 278(13): 11612-22.
Ferreira, S. T., M. N. Vieira, et al., "Soluble protein oligomers as emerging toxins in Alzheimer's and other amyloid diseases", (2007) *IUBMB Life* 59(4-5): 332-45.
Bitan, G., M. D. Kirkitadze, et al., "Amyloid β-protein (Aβ) assembly: Aβ40 and Aβ42 oligomerize through distinct pathways", (2003) *Proc Nati Acad Sci USA* 100(1): 330-5.

* cited by examiner

*Primary Examiner* — Kendra D Carter
(74) *Attorney, Agent, or Firm* — Ladas & Parry LLP

(57) ABSTRACT

Disclosed herein is a method for treating diseases associated with beta amyloid accumulation, including administering to a patient a therapeutically effective amount of morpholine or piperazine based compounds including a sulfuric or carboxylic acid structure represented by the following chemical formula 1 or a pharmaceutically acceptable salt thereof:

[Chemical Formula 1]

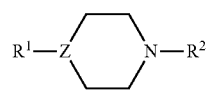

(wherein Z, $R^1$ and $R^2$ are as defined in the specification).

6 Claims, 13 Drawing Sheets

PHARMACEUTICAL COMPOSITION FOR PREVENTING OR TREATING DISEASES ASSOCIATED WITH BETA-AMYLOID ACCUMULATION CONTAINING MORPHOLIN OR PIPERAZINE BASED COMPOUNDS HAVING SO₃H OR COOH AS ACTIVE INGREDIENT

CROSS-REFERENCES TO RELATED APPLICATION

This patent application claims the benefit of priority from Korean Patent Application No. 10-2009-0123355, filed on Dec. 11, 2009, the contents of which are incorporated herein by reference.

BACKGROUND OF THE INVENTION

1. Field of the Invention

The present invention relates to a pharmaceutical composition for preventing or treating diseases associated with beta-amyloid accumulation containing morpholin or piperazine based compounds having $SO_3H$ or COOH as an active ingredient.

2. Description of the Related Art

As the global average life span of people increases and we see a transition to an aging society in which the population of elderly increases, the incidence rate of neurodegenerative diseases such as senile dementia represented by Alzheimer's disease, cerebral apoplexy, or Parkinson's disease has been greatly increased.

Dementia comprehensively include complex clinical symptoms from which a normally developed brain is impaired or destroyed by external factors such as trauma or diseases to abnormal cognitive impairments such as language, learning, intelligence, and etc. and higher mental functions, and progressive memory disorders bring disorders in social-vocational functions, accompanied by behavioral disorders such as aphasia, agnosia, apraxia, etc. Dementia may be largely divided into dementia by Alzheimer's disease, vascular dementia, dementia by specific neural diseases and systemic diseases, etc., and the dementia by Alzheimer's disease is responsible for 50% or more of them.

One of the anatomical characteristics of Alzheimer's disease is degeneration and death of nerve cells responsible for memory and cognition. One of the pathological characteristics is finding of neurofibrillary tangles within nerve cells and senile plaques outside nerve cells. Beta-amyloid deposits are discovered in the senile plaques, and it is usually known that they are in the form of fibril with a β-sheet structure, which is formed from beta-amyloid monomers. It is known that Alzheimer's disease is caused by various factor factors such as immunological factors, genetic factors, viral infection, toxic materials, damages, and etc. According to what has been known, it is reported that destruction of nerve cells by neurotoxicity of neural plaques produced from accumulation of beta-amyloid proteins in the brain and neurodegeneration by nerve fiber bundles produced from accumulation of hyperphosphorylated tau proteins in the brain are major causes of Alzheimer's dementia.

The beta-amyloid described above is a protein found in a patient with Alzheimer's disease, and a polypeptide consisting of 39-43 amino acid residues derived from amyloid protein precursor (APP) (Seubert, P., C. Vigo-Pelfrey, et al. (1992). "Isolation and quantification of soluble Alzheimer's beta-peptide from biological fluids." Nature 359(6393): 325-7., Shoji, M., T. E. Golde, et al. (1992). "Production of the Alzheimer amyloid beta protein by normal proteolytic processing." Science 258(5079):126-9., Busciglio, J., D. H. Gabuzda, et al. (1993). "Generation of beta-amyloid in the secretory pathway in neuronal and normeuronal cells." Proc Natl Acad Sci USA 90(5):2092-6). Amyloid protein precursor (APP) is degraded into beta-amyloid 40 or 42 (Aβ40 or Aβ42) monomer by β-secretase and γ-secretase, and then accumulated to form oligomers. The accumulation of these oligomers leads to a step of forming fibril. A strong neurotoxicity is exhibited in the brain from the state when the beta-amyloid in various steps becomes oligomers, leading to death of neuronal cells (Walsh, D. M., I. Klyubin, et al. (2002). "Naturally secreted oligomers of amyloid beta protein potently inhibit hippocampal long-term potentiation in vivo." Nature 416(6880):535-9., Stine, W. B., Jr., K. N. Dahlgren, et al. (2003). "In vitro characterization of conditions for amyloid-beta peptide oligomerization and fibrillogenesis." J Biol Chem 278(13):11612-22., Ferreira, S. T., M. N. Vieira, et al. (2007). "Soluble protein oligomers as emerging toxins in Alzheimer's and other amyloid diseases." IUBMB Life 59(4-5):332-45). Therefore, it is important to disaggregate the accumulated beta-amyloid or inhibit the accumulation of beta-amyloid for treatment of Alzheimer's disease.

The isoforms of beta-amyloid constituting most of the accumulated amyloids are beta-amyloids 40 and 42 consisting of 40 and 42 amino acids (Bitan, G., M. D. Kirkitadze, et al. (2003). "Amyloid β-protein (Aβ) assembly: Aβ40 and Aβ42 oligomerize through distinct pathways." Proc Natl Acad Sci USA 100(1):330-5), and glycosaminoglycan (GAG) and proteoglycan (PG) are materials which aid in the accumulation of the beta-amyloid among various factors involved in the accumulation of the amyloid. Glucosaminoglycan/proteoglycan present in cell membranes are combined with beta-amyloid and structurally changed to aid in the accumulation of beta-amyloid. In particular, the sulfate moieties portions of glucosaminoglycan/proteoglycan were reported to combine with the HHQK region corresponding to the 13rd-16th portion of 40 or 42 amino acids of beta-amyloid to serve as an important factor in the accumulation.

From the idea that a material called acetylcholine is decreased in the brains of patients with Alzheimer's disease when compared with normal subjects, there are drugs to be developed in the direction of increasing the quantity of acetylcholine in the brain or increasing the activity of cholinergic neurons as therapeutic agents currently developed. However, because commercially available drugs of these series such as donepezil, rivastigmin, galantamin, memantine, and etc. do not treat the disease fundamentally but rather improve cognitive functions, it is necessary to improve the agents to overcome their side effects and limitations.

Thus, the present inventors have performed research to develop therapeutic agents inhibiting the accumulation of beta-amyloid, found that morpholine or piperazine based compounds containing a sulfuric or carboxylic acid structures may inhibit the accumulation of beta-amyloid fibrils or oligomers, degrade the accumulated beta-amyloid fibrils and oligomers to inhibit the toxicity by beta-amyloid, and be useful as pharmaceutical compounds for prevention or treatment of diseases associated with beta-amyloid accumulation, for dementia including Alzheimer's disease, Down's syndrome, amyloid angiopathy, cerebral amyloid angiopathy, systemic amyloid disease, Dutch-type amyloidosis, and inclusion body myositis (IBM), and made the present invention.

SUMMARY OF THE INVENTION

The object of the present invention is to provide a pharmaceutical composition for preventing or treating diseases associated with beta-amyloid accumulation containing morpholin or piperazine based compounds having SO₃H or COOH.

In order to achieve the object, the present invention provides a pharmaceutical composition for preventing or treating diseases associated with beta-amyloid accumulation containing morpholin or piperazine based compounds having SO₃H or COOH represented by the following chemical formula 1,

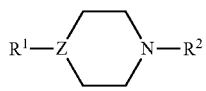

[Chemical Formula 1]

(wherein, Z, $R^1$ and $R^2$ are as defined in the disclosure.)

BRIEF DESCRIPTION OF THE DRAWINGS

FIG. 6 is a group of electron microscopic images illustrating the disaggregation degrees of beta-amyloid 40 aggregate of a compound of Formula 1a;

FIG. 7 is a group of electron microscopic images illustrating the disaggregation degrees of beta-amyloid 42 aggregate of a compound of Formula 1a;

DESCRIPTION OF THE PREFERRED EMBODIMENTS

Features and advantages of the present invention will be more clearly understood by the following detailed description of the present preferred embodiments by reference to the accompanying drawings. It is first noted that terms or words used herein should be construed as meanings or concepts corresponding with the technical sprit of the present invention, based on the principle that the inventor can appropriately define the concepts of the terms to best describe his own invention. Also, it should be understood that detailed descriptions of well-known functions and structures related to the present invention will be omitted so as not to unnecessarily obscure the important point of the present invention.

Hereinafter, the present invention will be described in detail.

The present invention provides a pharmaceutical composition for prevention or treatment of diseases associated with beta amyloid accumulation containing morpholine or piperazine based compounds including a sulfuric or carboxylic acid structure represented by the following Formula 1 as an active ingredient.

The present invention also provides a method for treating diseases associated with beta amyloid accumulation, including administering to a patient a therapeutically effective amount of morpholine or piperazine based compounds including a sulfuric or carboxylic acid structure represented by the following chemical formula 1 or a pharmaceutically acceptable salt thereof.

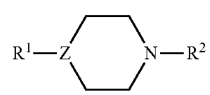

[Chemical Formula 1]

(wherein,

Z is O or N, $R^1$ is not bonded when Z=O, $R^1$ is —$(CH_2)_n$—OH when Z=N, $R^2$ is —$(CH_2)_n$—$R^3$, n is an integer of 1 to 5, and $R^3$ is COOH or $SO_3H$.)

Preferably, the compound of chemical formula 1 is selected from the group consisting of compounds following chemical formula 1a to 1e:

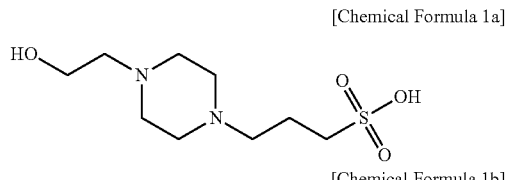

[Chemical Formula 1a]

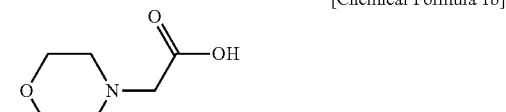

[Chemical Formula 1b]

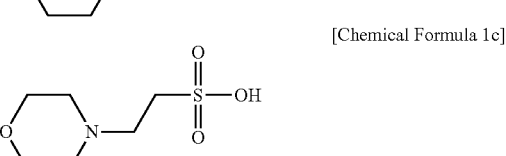

[Chemical Formula 1c]

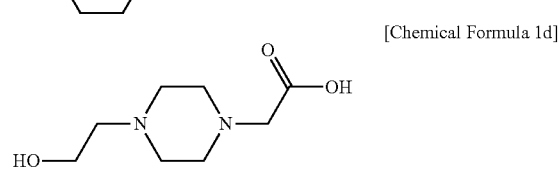

[Chemical Formula 1d]

-continued

[Chemical Formula 1e]

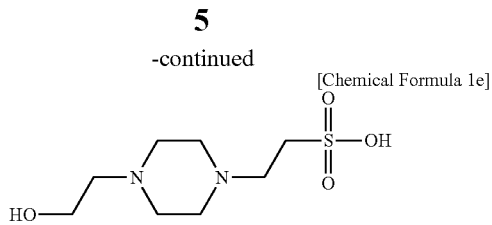

The diseases associated with beta amyloid accumulation include dementia including Alzheimer's disease, Down's syndrome, amyloid angiopathy, cerebral amyloid angiopathy, systemic amyloid disease, Dutch-type amyloidosis, inclusion body myositis (IBM), and etc.

Figure 1:
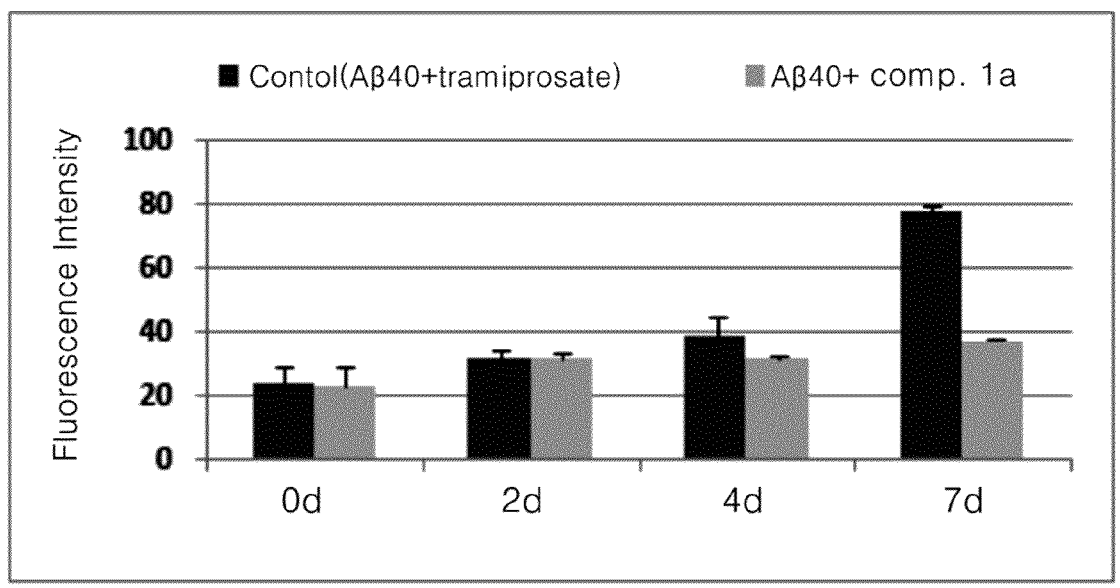
FIG. 1 is a graph illustrating the accumulation inhibitory degree of accumulated beta-amyloid by thioflavin T (ThT) fluorescence intensity of a compound of Formula 1a according to the present invention.

As a result of measurement experiments of beta-amyloid fibril accumulation inhibitory activity by thioflavin T (ThT) fluorescence intensity, it is determined that the compound of chemical formula 1 according to the present invention has the accumulation inhibitory activity on beta-amyloid by showing half of the fluorescence intensity compared to a control group treated with tramiprosate known as a compound which inhibits the accumulation of beta-amyloid (See Example 1 and FIG. 1).

Figure 2A:
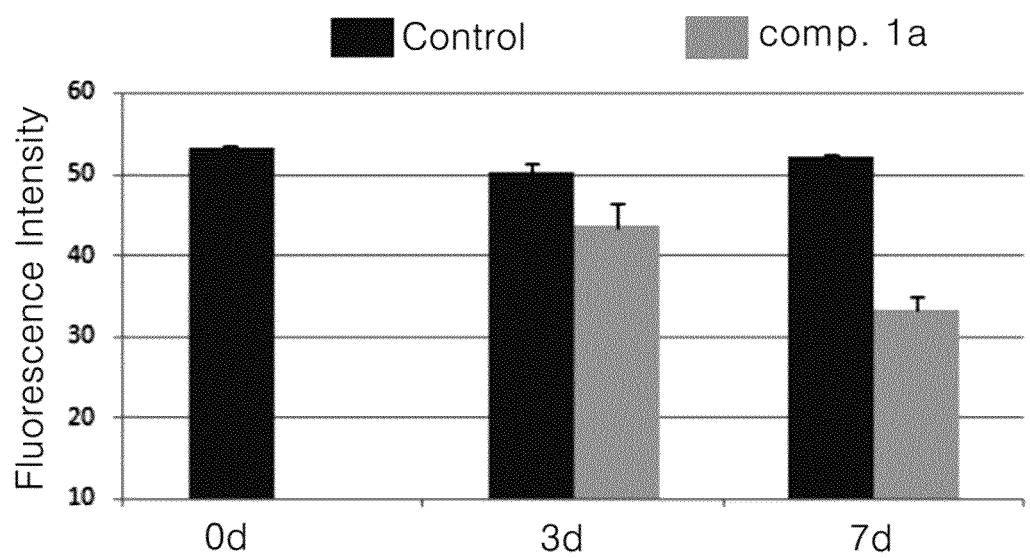
FIG. 2 is a group of graphs illustrating the disaggregation degrees of accumulated beta-amyloid by thioflavin T (ThT) fluorescence intensity of a compound of Formula 1a according to the present invention ((a) Aβ40 and (b) Aβ42)
Figure 2B:
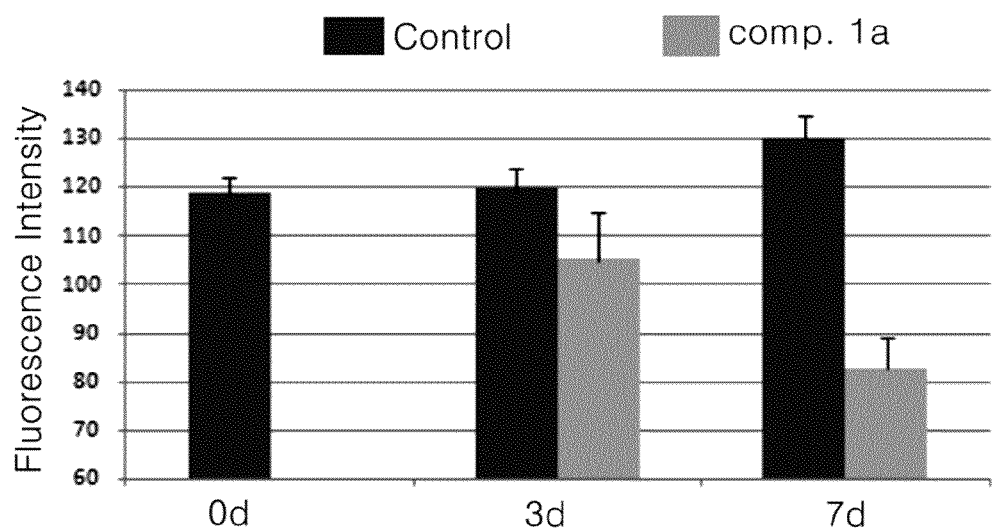
Figure 3:
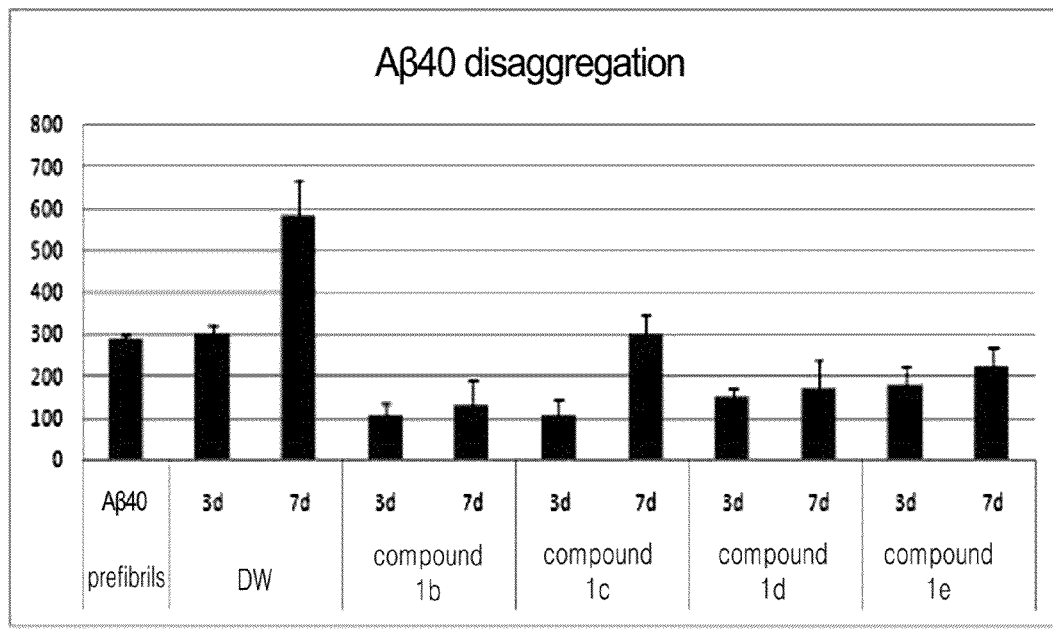
FIG. 3 is a graph illustrating the disaggregation degrees of accumulated beta-amyloid of Aβ40 by thioflavin T (ThT) fluorescence intensities of compounds of Formula 1b to 1e.

As a result of measurement experiments of beta-amyloid fibril disaggregation activity by thioflavin T (ThT) fluorescence intensity, it is determined that the compound of chemical formula 1 according to the present invention has the disaggregation activity of accumulated beta-amyloid by showing a lower fluorescence intensity compared to a control group (See Example 2 and FIGS. 2 and 3).

Figure 4A:
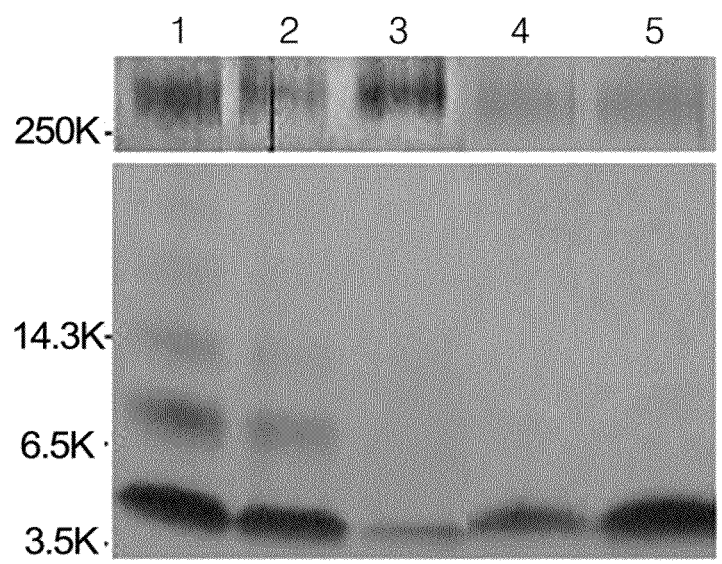
FIG. 4 is a group of electrophoresis images illustrating the disaggregation degrees of accumulated beta-amyloid by SDS-PAGE of a compound of Formula 1a (No. 1: initially formed beta-amyloid aggregate (prefibril), No. 2: 3rd day after a control group treatment, No. 3: 7th day after a control group treatment, No. 4: 3rd day after treatment with a compound of Formula 1a, and No. 5: 7th day after treatment with a compound of Formula 1a)
Figure 4B:
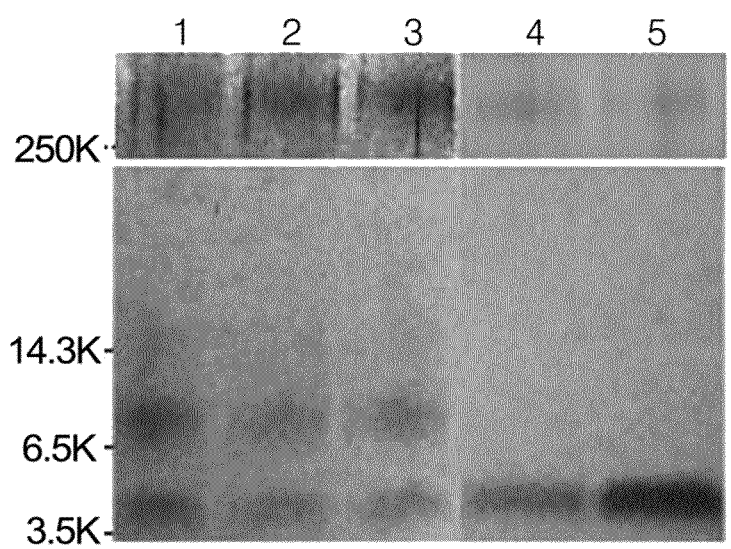
Figure 5:
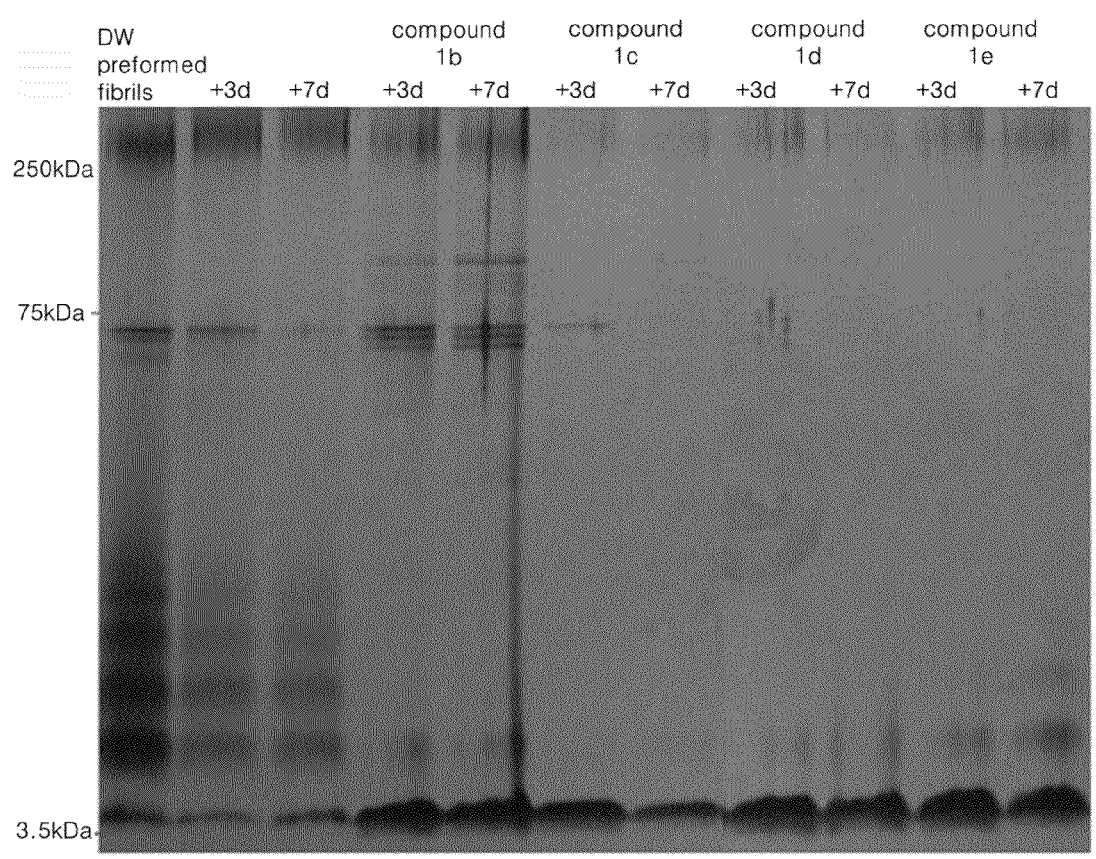
FIG. 5 is an electrophoresis image illustrating the disaggregation degree of accumulated beta-amyloid using the SDS-PAGEs of compounds of Formula 1b to 1e.

As a result of measurement experiments of beta-amyloid fibril disaggregation activity by SDS-PAGE, it is also determined that the compound of chemical formula 1 according to the present invention has the disaggregation activity of accumulated beta-amyloid by confirming that a band was shown near 4.3 kD corresponding to the size of Aβ40 monomer and beta-amyloid aggregates were disaggregated into monomers (See Example 3 and FIGS. 4 and 5).

Figure 6:
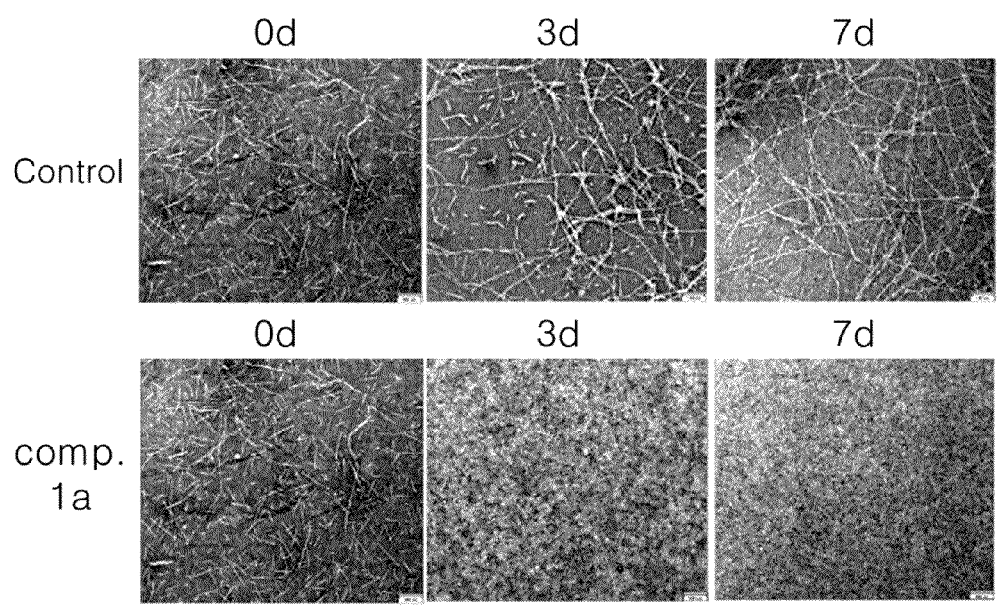
Figure 7:
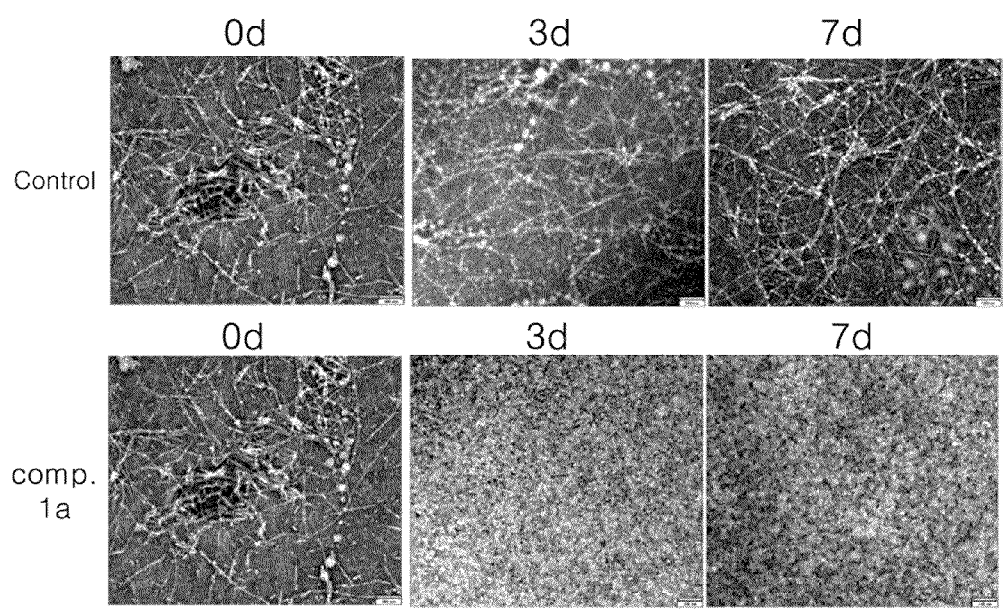

Furthermore, as a result of measurement experiments of beta-amyloid fibril disaggregation activity by electronic microscope, it is determined that the compound of chemical formula 1 according to the present invention has the disaggregation activity of accumulated beta-amyloid by observing that beta-amyloid fibril was not present (See Example 4 and FIGS. 6 and 7).

Figure 8A:
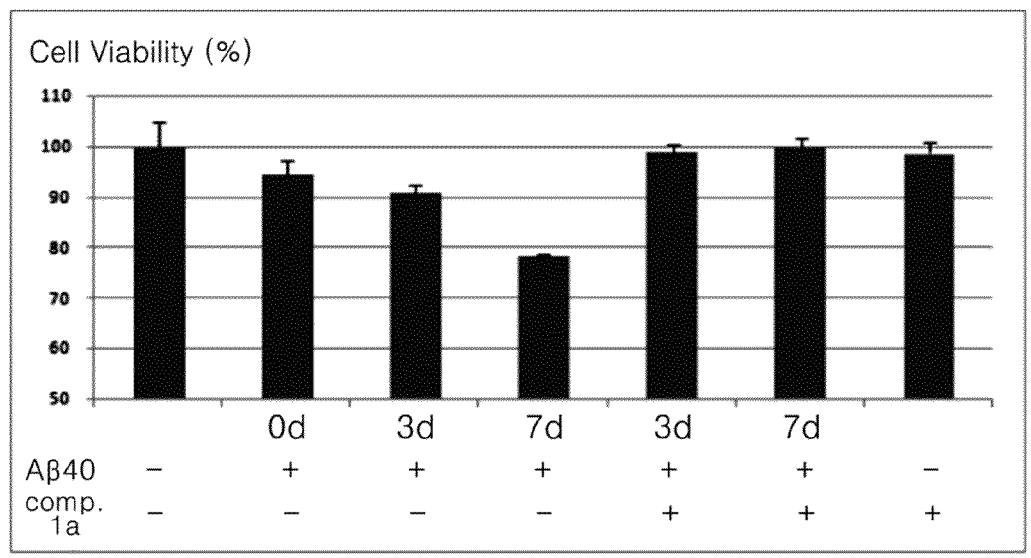
FIG. 8 is a group of graphs illustrating measurements of cell viabilities in order to determine the scavenging degrees of toxicity by beta-amyloid of a compound of Formula 1a ((a) Aβ40 and (b) Aβ42)
Figure 8B:
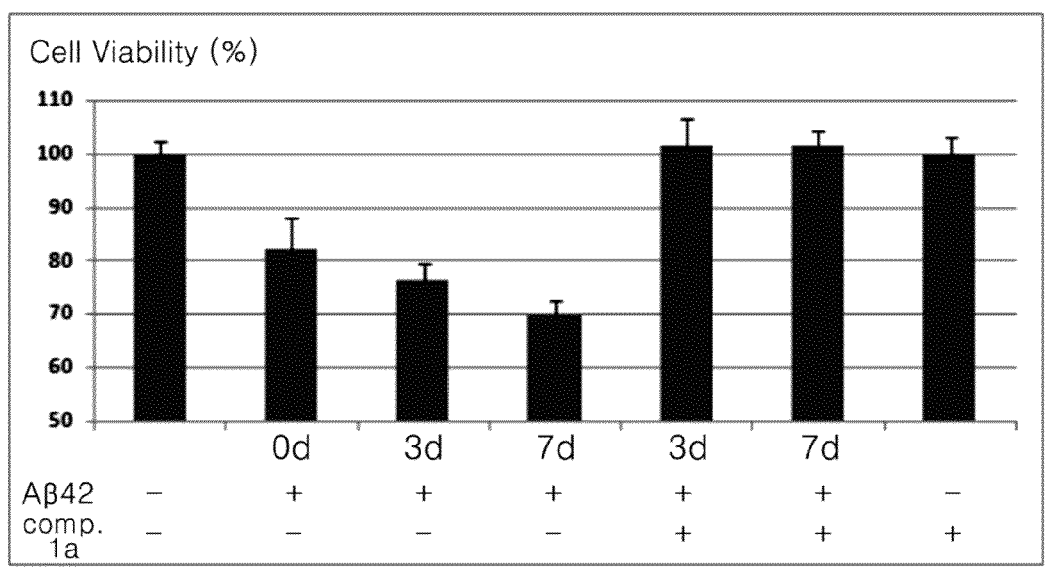

As a result of cytotoxicity tests of a compound of chemical formula 1 according to the present invention on beta-amyloid toxicity, it is determined that the treatment only with the compound resulted in 95% or more of cell viability, exhibited no toxicity to cells by significantly decreasing the toxicity of cells treated with beta-amyloid to increase the cell viability, and decreased the toxicity by the accumulated beta-amyloid while disaggregating the accumulation (See Example 5 and FIG. 8).

Thus, because the compound of chemical formula 1 according to the present invention may exhibit no toxicity to cells as well as decrease the toxicity by the beta-amyloid aggregates while inhibiting the accumulation of beta-amyloid and disaggregating the accumulated beta-amyloid, the compound may be useful as a compound for prevention or treatment of diseases associated with beta-amyloid accumulation.

When a compound of the present invention is used as a medicine, a pharmaceutical compound containing the compound represented by chemical formula 1 as an active ingredient may be prepared and administered in various oral or parenteral dosage forms as follows, but is not limited thereto.

Formulations for oral administration include, for example, tablets, pills, hard/soft capsules, liquid solutions, suspensions, emulsions, syrups, granules, elixirs, and etc. These formulations may contain, in addition to the active ingredient, diluents (e.g., lactose, dextrose, sucrose, mannitol, sorbitol, cellulose and/or glycine) and lubricants (e.g., silica, talc, stearic acid and magnesium or calcium salts thereof, and/or polyethylene glycol). Tablets may also contain binding agents such as magnesium aluminum silicate, starch paste, gelatin, methyl cellulose, sodium carboxymethylcellulose and/or polyvinylpyrrolidone, and if necessary, it may further contain disintegrators, e.g., starch, agar-agar, alginic acid or sodium salts thereof, or effervescent mixtures, and/or adsorption agents, colorants, flavoring agents and sweeteners.

A pharmaceutical composition for prevention or treatment of diseases associated with beta-amyloid accumulation containing the compound represented by chemical formula 1 as an active ingredient may be parenterally administered, and parenteral administration may be by subcutaneous, intravenous, intramuscular or intrasternal injection methods. In order to make a dosage form suitable for parenteral administration, the compound of chemical formula 1 should be mixed with stabilizers or buffers in water to prepare solutions or suspensions, which may be formulated in a unit dosage form of ampoules or vials.

The composition may be sterilized and/or contain adjuvants such as preservatives, stabilizers, wetting or emulsifying agents, salts for regulating the osmotic pressure and/or buffers, etc. and other therapeutically useful substances. The composition may be prepared according to conventional mixing, granulating or coating methods.

When a pharmaceutical composition for prevention or treatment of beta-amyloid aggregation-related disorders containing the compound represented by chemical formula 1 of the present invention as an active ingredient is formulated in a unit dosage form, it is preferable to contain the compound of chemical formula 1 in a unit dosage in the range of about 0.1 to 1,500 mg as an active ingredient. The dose should follow a doctor's prescription depending on factors such as the body weight and age of the patient and specific properties and severity of the disease. However, the dose required for treatment of an adult is usually in the range of about 1 mg/day to about 500 mg/day, depending on the frequency and intensity of administration. On intramuscular or intravenous administration into an adult, about 5 mg to about 300 mg per day may be sufficient as a separate one-time dosage. However, a larger amount may be preferable for some patients.

Hereinafter, the present invention will be described in more detail with reference to the following examples.

However, the following examples are provided for illustrative purposes only, and the scope of the present invention should not be limited thereto in any manner.

Example 1

Measurement Experiment of Beta-Amyloid Accumulation Inhibitory Activity by Thioflavin T (ThT) Fluorescence Intensity of a Composition According to the Present Invention In order to measure the beta-amyloid accumulation inhibitory activity of a compound according to the present invention, the following experiment was performed using thioflavin T (ThT) fluorescence intensity.

Thioflavin T (ThT) is well mixed with fibril which is a beta-amyloid aggregate in a solution and tends to increase the shifted fluorescence intensity as the concentration of fibril increases.

A solution was prepared in a DMSO solution such that Aβ40 might have a concentration of 5 mM, and diluted in a compound of chemical formula 1a by 100 times to prepare Aβ40 at a final concentration of 50 μM. The concentration of the compound was 20 mM. Tramiprosate was used as a control group. Tramiprosate is a compound known to treat Alzheimer's disease and related diseases by inhibiting the accumulation of beta-amyloid (F. Gervais, J. et al. (2007)). Subsequently, it was cultured at 37° C. for 7 days. On 0th, 2nd, 4th, and 7th day, 25 μl of reaction solution was aliquoted into each well, into which was added 75 μl of thioflavin T (ThT) to have thioflavin T (ThT) at a concentration of 5 μM. It was cultured for additional 15 minutes, and then the fluorescence intensity of a half well 96 fluorescence microplate was measured by Envision 2103 multilabel reader, Perkin-Elmer. During the measurement of fluorescence intensity, the wavelengths of excitation and emission were 450 nm and 485 nm, respectively and the counting time was 0.5 sec. The results are shown in FIG. 1.

As shown in FIG. 1, it is determined that the fluorescence intensity of a control group treated with tramiprosate known as a compound to inhibit the accumulation of beta-amyloid was increased by about 3.5 times while the fluorescence intensity of a group treated with a compound according to the present invention was increased by about 1.7 times. It is also determined that a group treated with a compound according to the present invention has excellent inhibitory effects of beta-amyloid by showing about half the fluorescence intensity of a control group treated with tramiprosate on 7th day.

From these, it is determined that the compound according to the present invention has an inhibitory activity of accumulation of beta-amyloid.

Example 2

Measurement Experiment of Accumulated Beta-Amyloid Disaggregation Activity by Thioflavin T (ThT) Fluorescence Intensity of a Composition According to the Present Invention In order to measure the disaggregation activity of the beta-amyloid aggregate of a compound according to the present invention, the following experiment was performed using thioflavin T (ThT) fluorescence intensity.

Thioflavin T (ThT) is well mixed with fibril which is a beta-amyloid aggregate in a solution and tends to increase the fluorescence intensity as the concentration of fibril increases.

For aggregation of beta-amyloid, a beta-amyloid stock solution was prepared. The beta-amyloid stock solutions were prepared in a DMSO solution such that Aβ40 or Aβ42 might have a concentration of 5 mM and 2.5 mM, respectively, and diluted in distilled water by 10 times to prepare Aβ40 and Aβ42 at a final concentration of 500 μM and 250 μM, respectively. It was cultured at 37° C. for 7 to 10 days to prepare a sufficient amount of beta-amyloid aggregate. Subsequently, compounds of chemical formula 1a to 1e according to the present invention or distilled water were again added into each accumulated beta-amyloid to obtain 10-times diluted solutions, and then they were cultured at 37° C. for 7 days. Distilled water was used as a control group. The final concentration of the compound was 20 mM, and the final concentrations of beta-amyloid Aβ40 or Aβ42 were 50 μM and 25 μM, respectively. After distilled water or the compound was added, 25 μl of each reaction solution on 0th, 3rd, and 7th day was aliquoted into each well, into which was added 75 μl of thioflavin T (ThT) to have thioflavin T (ThT) at a concentration of 5 μM. It was cultured for additional 15 minutes, and then the fluorescence intensity of a half well 96 fluorescence microplate was measured by Envision 2103 multilabel reader, Perkin-Elmer. During the measurement of fluorescence intensity, the wavelengths of excitation and emission were 450 nm and 485 nm, respectively and the counting time was 0.5 sec. The results are shown in FIGS. 2 and 3.

FIG. 2 (a) illustrates the fluorescence intensity of Aβ40 fibril when a compound of chemical formula 1a is added, FIG. 2 (b) illustrates the fluorescence intensity of Aβ42 fibril when a compound of chemical formula 1a is added, and FIG. 3 illustrates the fluorescence intensities of Aβ40 fibril when compounds of chemical formula 1b to 1e are added.

As shown in FIGS. 2 and 3, it is determined that the fluorescence intensity of a control group treated with distilled water was equivalent to those of a initially formed aggregates (prefibrils) or increased over time while a group treated with a compound according to the present invention exhibited a fluorescence intensity less than high fluorescence intensities of initially prepared fibrils and the fluorescence intensity of a compound of chemical formula 1a (FIG. 2) was increased over time. Because the decrease of fluorescence intensity means that the amount of fibril decreases, it is determined that the compound according to the present invention disaggregates the accumulated beta-amyloid.

Example 3

Measurement of Beta-Amyloid Fibril Disaggregation Activity of a Compound of the Present Invention by SDS-PAGE In order to measure the accumulated beta-amyloid disaggregation activity of a compound according to the present invention, the following experiment was performed using SDS-PAGE.

Although the amount of fibril may be observed by a method using thioflavin T (ThT) fluorescence intensity, it is impossible to directly confirm that beta-amyloid fibril is disaggregated into monomers. Thus, SDS-PAGE was performed in order to observe whether beta-amyloid fibril could be disaggregated into monomers.

When peptides or proteins are subjected to electrophoresis on an SDS gel, the secondary structures of the proteins are broken. Thus, it is necessary to cross-link the proteins and immobilize their structures. It is achieved by a photo-induced cross-linking such that the structure of accumulated beta-amyloid may not be dismissed during electrophoresis on SDS gel. Specifically, a beta-amyloid stock solution was prepared in a DMSO solution such that Aβ40 or Aβ42 may have a concentration of 5 mM or 2.5 mM, and was distilled by 10 times using distilled water to prepare Aβ40 and Aβ42 at a concentration of 500 μM and 250 μM, respectively. It was cultured at 37° C. for 7 to 10 days to prepare a sufficient amount of beta-amyloid aggregate. Subsequently, compounds of chemical formula 1a to 1e according to the present invention or distilled water were again added into each accumulated beta-amyloid to obtain 10-times diluted solutions, and then they were cultured at 37° C. for 7 days. Distilled water was used as a control group. The final concentration of the compound was 20 mM, and the final concentrations of beta-amyloid Aβ40 or Aβ42 were 50 μM and 25 μM, respectively. 20 μl of reaction solution on 0th, 3rd, and 7th day after addition of distilled water or the compound was placed into each transparent tube with thin wall, into which was added each 1.5 µl of ammonium persulfate (APS) and Ru(II)(tris(2, 2'-bipyridyl)dichlororuthenium (II), and then the mixture was exposed to light three to five times for each second. When protein is exposed to light, the secondary structure of protein is permanently immobilized and it is possible to maintain the structure even in the SDS solution. A reaction solution cross-linked through the steps was subjected to electrophoresis on 10-20% tris-tris gel (gradient gel, Criterion™ PrecastGel, BIO-RAD) or 16.5% tris-tricine gel (Criterion™ PrecastGel, BIO-RAD) with 1.0 mm thickness at 120 V for one hour to 2 hours 20 min. After electrophoresis, the gel was silver stained (silver staining kit-Amersham Biosciences) to observe the band. SPD-PAGE analysis results in Aβ40 and Aβ42 are shown in FIGS. 4 and 5.

FIG. 4(a) is an SDS-PAGE analysis result illustrating the disaggregation of accumulated Aβ40 when a compound of chemical formula 1a was added, FIG. 4(b) is an SDS-PAGE analysis result illustrating the disaggregation of accumulated Aβ40 when a compound of chemical formula 1b was added, and FIG. 5 is an SDS-PAGE analysis result illustrating the disaggregation of accumulated Aβ40 when compounds of chemical formula 1a to 1e were added.

As shown in FIG. 4, it is determined that accumulated beta-amyloid was disaggregated into monomers from the results that Aβ40 and Aβ42 were present in the accumulated forms as a band appeared near about 250 kD in a control group (No. 1: 0th day (prefibrils), No. 2: 3rd day, and No. 3: 7th day) treated with distilled water while a band appeared near 3.5 kD corresponding to the size of monomers of Aβ40 and Aβ42 in Aβ40 and Aβ42.

As shown in FIG. 5, it is determined from treatment results with compounds of chemical formula 1b to 1e according to the present invention that as the intensity of a band near 3.5 kD corresponding to the size of monomer of Aβ40 increased and the intensity of a band of the aggregate appearing above decreased, beta-amyloid accumulated from these was disaggregated into monomers.

Therefore, it is determined that the compound according to the present invention has an activity to disaggregate accumulated beta-amyloid species.

Example 4

Measurement of Beta-Amyloid Fibril Disaggregation Activity of a Compound of the Present Invention by Electronic Microscope In order to measure accumulated beta-amyloid disaggregation activity of a compound according to the present invention, the following experiment was performed using electronic microscope.

A beta-amyloid stock solution was prepared such that Aβ40 or Aβ42 might have a concentration of 5 mM and 2.5 mM, respectively, and diluted in distilled water by 10 times to prepare Aβ40 and Aβ42 at a final concentration of 500 µM and 250 µM, respectively. It was cultured at 37° C. for 7 to 10 days to prepare a sufficient amount of beta-amyloid aggregate. Subsequently, compounds of chemical formula 1a to 1e according to the present invention or distilled water were again added into each accumulated beta-amyloid to obtain 10-times diluted solutions, and then it was cultured at 37° C. for 7 days. Distilled water was used as a control group. The final concentration of the compound was 20 mM, and the final concentrations of beta-amyloid Aβ40 or Aβ42 were 50 µM and 25 µM, respectively. Subsequently, a compound of chemical formula 1a was added, and then the mixture was cultured at 37° C. for 7 days. From each of the reaction solutions on 0th, 3rd, and 7th days after addition of distilled water or the compound, the accumulations and disaggregation degrees of accumulated beta-amyloid were observed using analytical transmission electron microscope. FIG. 6 illustrates electronic microscopic images of Aβ40, and FIG. 7 illustrates electronic microscopic images of Aβ42.

As shown in FIGS. 6 and 7, it is determined that long thread-like beta-amyloid fibrils appeared on 0th day in a group treated with a compound of chemical formula 1a according to the present invention, while no beta-amyloid fibrils appeared on 3rd and 7th days. It is determined that long thread-like beta-amyloid fibrils appeared on 0th day in a control group treated with distilled water, while a number of aggregates were formed as the lengths of beta-amyloid on 3rd and 7th days continued to increase.

It is determined from these that a compound according to the present invention has an activity of disaggregating beta-amyloid aggregates.

Example 5

Test of Cytotoxicity of a Compound According to the Present Invention on Beta-Amyloid Toxicity In order to determine the cell survival rate of a compound according to the present invention on beta-amyloid toxicity, the following example was performed.

In order to obtain beta-amyloid aggregates, a beta-amyloid stock solution was prepared. The beta-amyloid stock solutions were prepared in a DMSO solution such that Aβ40 or Aβ42 might have a concentration of 5 mM and 2.5 mM, respectively, and diluted in distilled water by 10 times to prepare Aβ40 and Aβ42 at a final concentration of 500 µM and 250 µM, respectively. Distilled water added to each solution to culture a 10 times diluted beta-amyloid at 37° C. for 7 to 10 days. Subsequently, compounds of chemical formula 1a to 1e according to the present invention or distilled water were again added into each beta-amyloid to obtain 10-times diluted solutions, and then it was cultured at 37° C. for 7 days. Distilled water was used as a control group instead of the compound. The final concentration of the compound was 20 mM, and the final concentrations of beta-amyloid Aβ40 or Aβ42 were 50 µM and 25 µM, respectively. Next, a compound of chemical formula 1a was added, and the mixture was cultured at 37° C. for 7 days. The cytotoxicity of the reaction solutions on 0th, 3rd, and 7th days after addition of distilled water or the compound was measured using the following cell line.

HT-22, a neuronal cell line of a rat, was cultured in DMEM (Dulbecco's Modified Eagle's Medium) supplemented with 10% FBS (Fetal Bovine Serum) and 1% penicillin/streptomycin in an incubator of 37° C. and 5% $CO_2$. Prior to the experiment, the HT-22 cell was plate-cultured at $3 \times 10^3$ cell/well in a 96 well plate and then cultured in a DMEM medium in which serum was removed (FBS 2%) overnight. The beta-amyloid aggregate prepared above was added and cultured. The solution added in the beta-amyloid cell was treated with Aβ40 and Aβ42 at 2 µM and 1 µM, and then cultured for 24 hours to induce necrosis by the toxicity of beta-amyloid. 10 µl of an MTT solution at 5 mg/µl was placed into each well and cultured for 4 hours, and then into the culture was added 100 µl of solubilization buffer for reaction. 18 hours later, the optical absorption was determined at 570 nm by a microplate reader. Living cells without any treatment were converted into 100% for comparison, and then the results are shown in FIG. 8. FIG. 8 (a) illustrates the cell viability when Aβ40 was used, and FIG. 8 (b) illustrates the cell viability when Aβ42 was used.

As shown in FIGS. 8 (a) and (b), it is determined that the cytotoxicity was decreased by about 70% to exhibit the cytotoxicity of beta-amyloid when beta-amyloid was treated while the cell viability was maintained at 95% or more by significantly decreasing the toxicity of cells treated with beta-amyloid when cells are treated with a compound of chemical formula 1a according to the present invention. It is also determined that a compound according to the present invention exhibited 95% or more of cell viability even without any treatment of beta-amyloid not to cause any toxicity to cells.

From these, it is determined that a compound according to the present invention does not exhibit toxicity to cells as well as decreases the toxicity by the accumulation of beta-amyloid while degrading the accumulation.

Comparative Example

Measurement Experiment of Disaggregation Activity of Beta-Amyloid Aggregation by Thioflavin T (ThT) Fluorescence Intensity of a Compound According to a Conventional Technology A measurement experiment of disaggregating activity of accumulation of beta-amyloid to Aβ40 and Aβ42 was performed with a HEPPSO compound of the following chemical formula 2 disclosed in U.S. Pat. No. 7,244,764 (2007. Jan. 17) in the same manner as in Example 2, and the results are shown in FIG. 9.

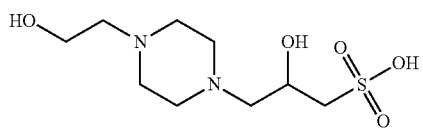

[Formula 2]

Figure 9A:
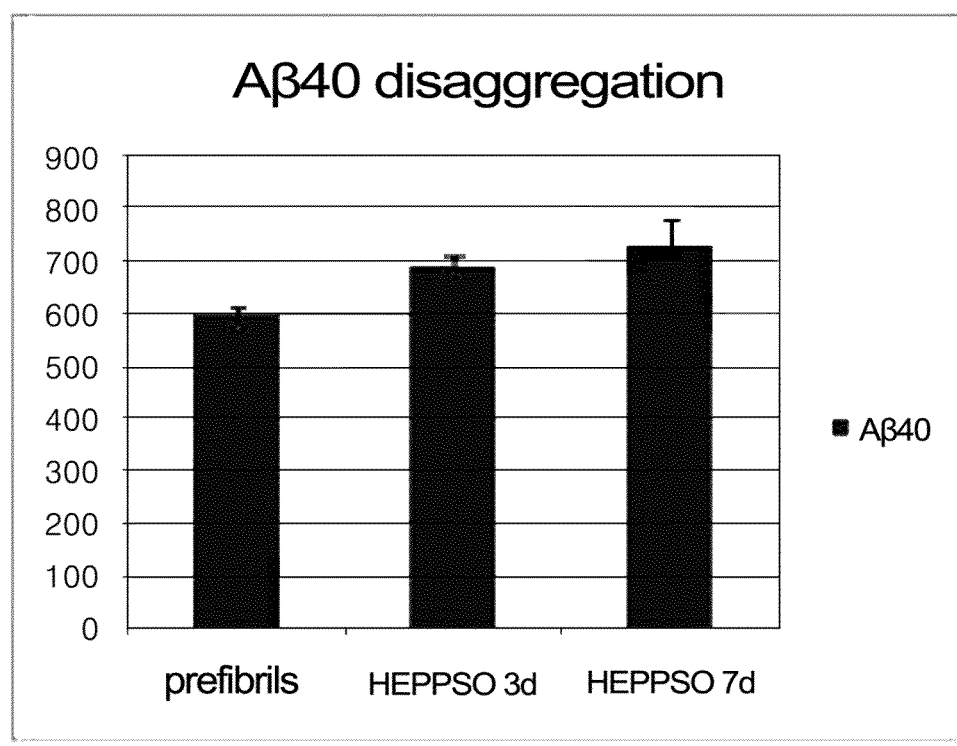
FIG. 9 is a group of graphs illustrating the disaggregation degrees of accumulated beta-amyloid by thioflavin T (ThT) fluorescence intensity of a compound of Formula 2 according to a conventional technology.
Figure 9B:
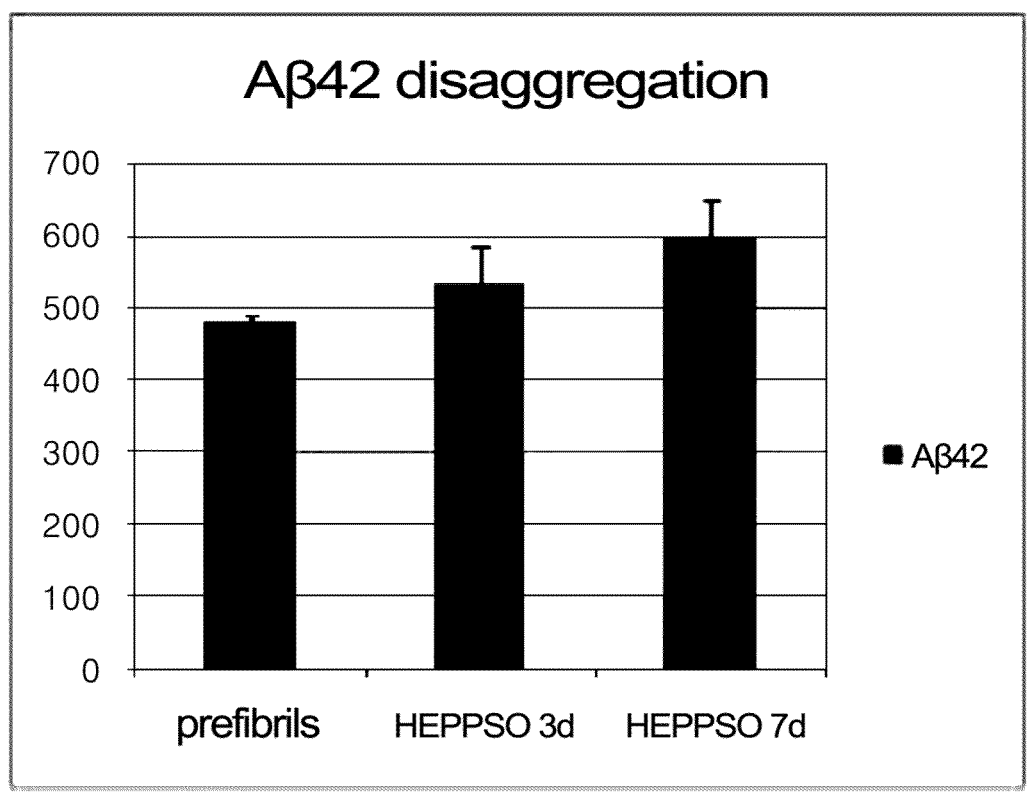

As shown in FIG. 9, it is determined that the fluorescence intensity was increased when treated with a compound of the above chemical formula 2 compared to that of an aggregate initially prepared (prefibrils). Thus, it is determined that a compound of the above Formula 2 does not exhibit any disaggregation activity to the beta-amyloid aggregate.

Therefore, because the compound according to the present invention does not exhibit any toxicity to cells as well as may inhibit the accumulation of beta-amyloid and disaggregate the accumulated beta-amyloid to inhibit the toxicity by beta-amyloid, it may be useful as a pharmaceutical composition for prevention or treatment of diseases associated with beta-amyloid accumulation, such as dementia including Alzheimer's disease, Down's syndrome, amyloid angiopathy, cerebral amyloid angiopathy, systemic amyloid disease, Dutch-type amyloidosis, and inclusion body myositis (IBM).

A compound represented by the above chemical formula 1 according to the present invention may be prepared in various forms according to its purposes. The following is provided only to illustrate some preparation methods of a compound represented by the above Formula 1, which is contained as an active ingredient, and the present invention is not limited thereby.

Preparation Example 1

Preparation of Powders

| Compound of chemical formula 1 | 2 g |
| Lactose | 1 g |

The ingredients were mixed and filled into sealed packaging to provide powders.

Preparation Example 2

Preparation of a Tablet

| Compound of chemical formula 1 | 100 mg |
| Corn starch | 100 mg |
| Lactose | 100 mg |
| Magnesium stearate | 2 mg |

The ingredients were mixed and tabletted according to a conventional tablet preparation method to provide a tablet.

Preparation Example 3

Preparation of a Capsule

| Compound of chemical formula 1 | 100 mg |
| Corn starch | 100 mg |
| Lactose | 100 mg |
| Magnesium stearate | 2 mg |

The ingredients were mixed and filled into a gelatin capsule according to a conventional capsule preparation method to provide a capsule.

Preparation Example 4

Preparation of Injections

| Compound of chemical formula 1 | 100 mg |
| Mannitol | 100 mg |
| $Na_2HPO_4 \cdot 2H_2O$ | 26 mg |
| Distilled water | 2974 mg |

The ingredients were contained as in the contents presented according to a conventional injection preparation method to provide injections.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method for treating diseases associated with beta amyloid accumulation, including administering to a patient a therapeutically effective amount of the following chemical formula 1a or a pharmaceutically acceptable salt thereof:

[Chemical Formula 1a]

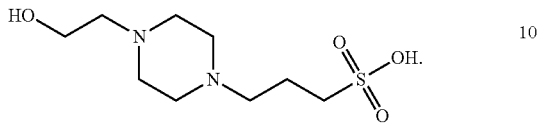

2. The method as set forth in claim 1, wherein the diseases associated with beta amyloid accumulation comprises Alzheimer's disease.

3. The method as set forth in claim 1, wherein the compound of chemical formula 1a has an inhibitory activity of accumulation of beta-amyloid.

4. The method as set forth in claim 1, wherein the compound of chemical formula 1a has an activity to disaggregate accumulated beta-amyloid aggregates.

5. The method as set forth in claim 1, wherein the compound of chemical formula 1a does not exhibit toxicity to cells.

6. The method as set forth in claim 1, wherein the compound of chemical formula 1a decreases the toxicity by the accumulation of beta-amyloid.

* * * * *